United States Patent
Omori et al.

(10) Patent No.: US 10,945,939 B2
(45) Date of Patent: Mar. 16, 2021

(54) OIL COMPOSITION, PRODUCTION METHOD THEREOF, OILY BASE AND EXTERNAL PREPARATION FOR SKIN

(71) Applicant: YOKOZEKI OIL & FAT INDUSTRIES CO., LTD., Kitaibaraki (JP)

(72) Inventors: Minoru Omori, Kitaibaraki (JP); Chisato Obana, Kitaibaraki (JP); Mamiko Suzuki, Kitaibaraki (JP)

(73) Assignee: YOKOZEKI OIL & FAT INDUSTRIES CO., LTD., Kitaibaraki (JP)

(*) Notice: Subject to any disclaimer, the term of this patent is extended or adjusted under 35 U.S.C. 154(b) by 0 days.

(21) Appl. No.: 16/485,820

(22) PCT Filed: Feb. 9, 2018

(86) PCT No.: PCT/JP2018/004709
§ 371 (c)(1),
(2) Date: Aug. 14, 2019

(87) PCT Pub. No.: WO2018/151054
PCT Pub. Date: Aug. 23, 2018

(65) Prior Publication Data
US 2020/0054542 A1 Feb. 20, 2020

(30) Foreign Application Priority Data
Feb. 15, 2017 (JP) .............................. JP2017-025668

(51) Int. Cl.
*A61K 8/63* (2006.01)
*A61K 8/25* (2006.01)
*A61K 8/31* (2006.01)
*A61K 8/34* (2006.01)
*A61K 8/36* (2006.01)
*A61Q 1/06* (2006.01)
*A61Q 5/06* (2006.01)

(52) U.S. Cl.
CPC .................. *A61K 8/63* (2013.01); *A61K 8/25* (2013.01); *A61K 8/31* (2013.01); *A61K 8/34* (2013.01); *A61K 8/361* (2013.01); *A61Q 1/06* (2013.01); *A61Q 5/06* (2013.01); *A61K 2800/262* (2013.01); *A61K 2800/522* (2013.01); *A61K 2800/54* (2013.01)

(58) Field of Classification Search
None
See application file for complete search history.

(56) References Cited

U.S. PATENT DOCUMENTS

| 3,926,936 A | 12/1975 | Lehtinen |
| 2008/0015367 A1* | 1/2008 | Dobbins ............... C11C 3/003 549/407 |

FOREIGN PATENT DOCUMENTS

| JP | S49-133313 A | 12/1974 |
| JP | 2001-048728 A | 2/2001 |
| JP | 2003-226609 A | 8/2003 |
| JP | 2005-239556 A | 9/2005 |
| JP | 2009-242305 A | 10/2009 |
| JP | 2016-190792 A | 11/2016 |

OTHER PUBLICATIONS

Apr. 3, 2018 International Search Report issued in International Patent Application No. PCT/JP2018/004709.
J. Terao. "Theory of Peroxidation Reaction of Fats and Oils." Journal of Cookery Science of Japan. vol. 28, No. 3. Aug. 20, 1995, pp. 46-51 (190-195).
A. Kamal-Edin. Ed. F. Shahidi. "Minor Components of Fats and Oils." Bailey's Industrial Oil and Fat Products, Sixth Edition. John Wiley & Sons, Inc., Apr. 2005, pp. 319-359.
Aug. 20, 2019 International Preliminary Report on Patentability issued in International Patent Application No. PCT/JP2018/004709.

* cited by examiner

*Primary Examiner* — Brian J Davis
(74) *Attorney, Agent, or Firm* — Oliff PLC

(57) ABSTRACT

An oil composition containing 70 to 100% by mass of an oil composition (A) which is mainly composed of a steradiene having a 3, 5-conjugated diene structure formed by dehydrating a hydroxyl group at 3-C of phytosterol, while having a phytosterol content of 20% by mass or less, and which is liquid at 25° C., and 0 to 30% by mass of an oil (B) which is soluble in the oil composition (A) has excellent transparency and gloss imparting property, and is useful as an oily base to produce an external preparation for skin. An external preparation for skin which contains the oil composition as an oil base is excellent in gloss and adhesion. The content of the steradiene in the oil composition (A) is usually 60% by mass or more, and is preferably 95% by mass or more.

13 Claims, No Drawings

OIL COMPOSITION, PRODUCTION METHOD THEREOF, OILY BASE AND EXTERNAL PREPARATION FOR SKIN

TECHNICAL FIELD

The present disclosure relates to an oil composition containing a steradiene obtained by dehydrating a hydroxyl group of phytosterol as a main component, a production method thereof, an oily base composed of the oil composition for producing an external preparation for skin, and an external preparation for skin containing the oily base.

BACKGROUND

Phytosterols, which are also called plant sterols, are minor components contained in vegetable oils such as soybean oil and rapeseed oil, and are a group of compounds classified as sterols (steroid alcohols). The phytosterols are generally white solids having unique odor, and are known to be useful as an additive for food additives, pharmaceuticals or cosmetics. For example, Patent Document 1 discloses a cosmetic containing a phospholipid such as soybean phospholipid and a phytosterol. Patent Document 2 discloses a composition for a cosmetic or an external preparation that contains an ester having a melting point 30 to 70° C. derived from an alcohol component containing phytosterols and a dimer acid. Thus, phytosterols and derivatives thereof have been conventionally known to be useful. However, there is a problem that they are difficult to handle (as compared to a liquid material) when used as an ingredient of a cosmetic since they are generally solid or pasty at room temperature. Recently, phytosterol derivatives that are liquid at room temperature have been commercially available, but a number of commercial products is still limited.

Further, phytosterol esters have gloss imparting property that is equal to or more as compared with lanolin that has been preferably used as a gloss imparting agent in the field of cosmetics. But, there is a demand to develop a material having more excellent gloss imparting property in the field of recent cosmetics. Also, phytosterol esters have another problem that they are not suitable for applications requiring transparency since many thereof are colored.

On the other hand, Non-Patent Document 1 discloses that, in the purification process of vegetable oils, conversion to 3,5-conjugated diene structure via detachment reaction of a hydroxyl group at 3-C of phytosterol may occur depending on conditions of the purification, and that the reaction product is referred to as steradiene. However, there is little report on steradiene, and little is known about physical properties of steradiene and suitability as a component for cosmetics.

Above-Mentioned Patent Documents

Patent Document 1: JP Patent No. 5576028
Patent Document 2: JP Patent No. 3826057
Above-mentioned non-patent document:
Non-Patent Document 1: Bailey's Industrial Oil and Fat Products, Sixth Edition, Six Volume Set (pp. 319 to 359).

SUMMARY

The embodiments of the invention of the present disclosure have been completed under such a background art. The present disclosure aims to create an oily material suitable as an additive for an external preparation for skin from phytosterols with a good reputation for safety that are derived from vegetable oils, in particular, to provide a transparent oil composition with excellent gloss imparting property. Another object is to provide a method for efficiently producing the oil composition. One of other objects is to provide an oily base composed of the oil composition, and the other object is to provide an external preparation for skin containing the oily base.

The present inventors have intensively studied to solve the above problems, and have found that steradiene having 3, 5-conjugated diene structure formed via detachment reaction of a hydroxyl group at 3-C of phytosterol which is industrially available is a mixture of a plurality of steradiene compounds, that the mixture is an oil at room temperature, and that the oil composition exhibits excellent gloss imparting property when used as an oily base of an external preparation for skin. Further, the present inventors have found that a mixture of the oil composition and an appropriate amount of other oil being soluble therein is more excellent in storage stability as compared with the oil composition per se while maintaining the advantages of the oil composition. The embodiments described in the present disclosure have been completed based on the above knowledge.

Thus, the present disclosure provides, as a first embodiment, an oil composition comprising 70 to 100% by mass of an oil composition (A) that contains a steradiene having a 3,5-conjugated diene structure obtained by dehydrating a hydroxyl group at 3-C of phytosterol as a main component, has a phytosterol content of 20% by mass or less, and is liquid at 25° C., and 0 to 30% by mass of an oil (B) that is soluble in the oil composition (A). Further, the present disclosure provides, as a secondary embodiment, a method for producing an oil composition wherein a phytosterol is heated in the presence or absence of a dehydration catalyst, and optionally mixed with the oil (B) and/or an oil-soluble antioxidant (C). The present disclosure also provides, as a third embodiment and a fourth embodiment, an oily base composed of the oil composition for an external preparation for skin and an external preparation for skin containing the oily base, respectively.

The oil composition (A) of the present disclosure containing steradienes as a main component is excellent in safety since it is obtained by modifying phytosterols with a good reputation for safety which are derived from vegetable oils. The oil composition (A) is light in color and excellent in transparency, and is also excellent in gloss imparting property due to a larger refractive index as compared with conventionally known phytosterol derivatives. Further, the oil composition (A) is excellent in absorption capacity of UV-C having a short wavelength. Use of the oil composition (A) as an oily base of an external preparation for skin enables the oily base to be readily handled upon preparing the external preparation, and the external preparation for skin thus obtained is excellent in adhesion and water retention property as well as gloss. Moreover, a mixture of the oil composition (A) and an appropriate amount of other oil being soluble therein (B) is more excellent in storage stability as compared with the oil composition (A) per se while maintaining the advantages of the oil composition (A).

DETAILED DESCRIPTION OF EMBODIMENTS

Hereinafter, some embodiments of the present disclosure will be described in detail.

<Oil Composition Composed of Steradiene (A)>

The oil composition (A) of the present disclosure is a mixture that is liquid at 25° C. and contains preferably two or more steradiens. Here, the term "steradien" means a dehydrated phytosterol having a 3, 5-diene structure formed via detachment of a hydroxyl group at 3-C of phytosterol. Phytosterol has a structure similar to the structure formula of cholesterol represented by the following formula (1). Phytosterol differs from cholesterol in formation of double bond between 5-C and 6-C, existence of a substituent at 24-C, and possible formation of double bond between 22-C and 23-C.

(Formula 1)

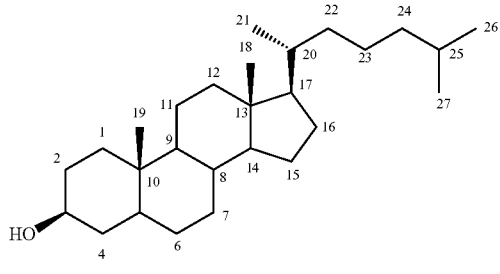

Cholesterol

A Representative example of phytosterols is sitosterol, i.e., Stigumasta-5-en-3β-ol represented by formula (2) that has a structure with two carbon atoms added to 24-C of cholesterol (i.e., ethyl substituent having an ethyl group at 24-C). Removal of one carbon atom at 24-C of sitosterol (i.e., methyl substituent) makes campesterol represented by formula (3) (campesta-5-en-3β-ol). Formation of a C═C double bond by removing hydrogen atoms at 22-C and 23-C of sitosterol makes stigmasterol (22E)-stigumasta-5, 22-diene-3-ol) represented by formula (4). Removal of one carbon atom at 24-C and formation of a C═C double bond by removing hydrogen atoms at 22-C and 23-C make brassicasterol ((22E)-ergosta-5,22-diene-33-ol) represented by formula (5).

(Formula 2)

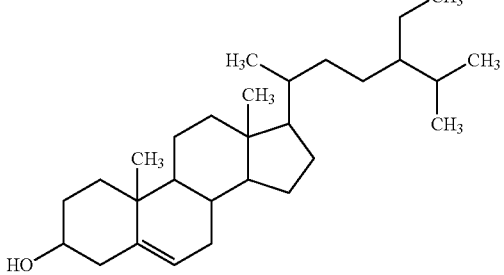

Sitosterol (Formula 3)

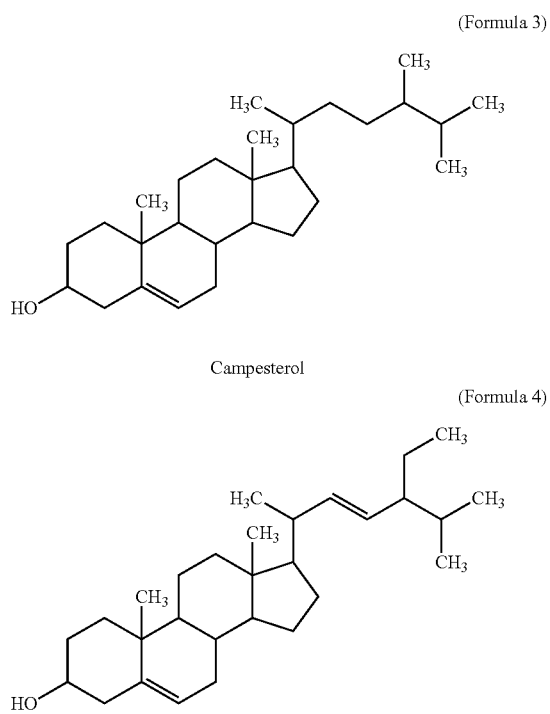

Campesterol (Formula 4)

Stigmasterol (Formula 5)

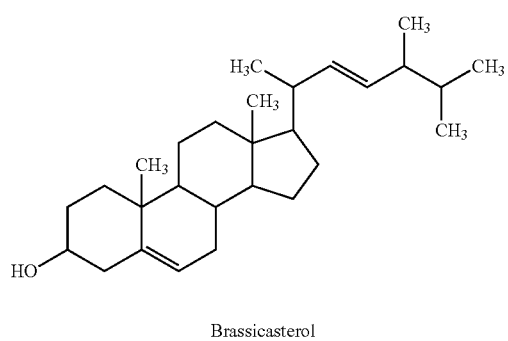

Brassicasterol

Steradien in the present disclosure is a dehydrated phytosterol having a 3, 5-diene structure formed via detachment of a hydroxyl group at 3-C of phytosterol, and each steradien corresponding to sitosterol, campesterol, stigmasterol or brassicasterol is respectively referred to as citosteradiene, campesteradiene, stigmasteradiene or brassicasteradiene. Structure formulae of these compounds are the same as formulae 2 to 5 except that a double bond is formed between 3-C and 4-C.

As used in the present specification, the terms "phytosterol" and "steradiene" are sometimes used as a generic term for indicating a group of compounds, and are sometimes used as a term for indicating a single compound. In the following description, the oil compositions of the present disclosure are sometimes referred to as "steradiene oil".

Phytosterols are generally separated as a by-product in the step of obtaining a desired fatty acid from vegetable oils. Ingredients of phytosterols and compositions thereof are different depending on the type of vegetable oils. Each of the ingredients is difficult to isolate as a single component since molecular weight and boiling point thereof are very close to each other. Hence, phytosterols are usually obtained as a mixture containing a plurality of phytosterols.

For example, phytosterol derived from soybean oil is a solid oil that usually contains 40 to 60% by mass of β-sitosterol, 10 to 20% by mass of campesterol, 20 to 30% by mass of stigmasterol, and 0 to 3% by mass of brassicasterol. Phytosterols derived from rapeseed oil is a solid oil that usually contains 40 to 60% by mass of β-sitosterol, 10 to 20% by mass of campesterol, 0 to 3% by mass of stigmasterol, and 10 to 20% by mass of brassicasterol. Phytosterol derived from sunflower oil is a solid oil that usually contains 70 to 80% by mass of β-sitosterol, 10 to 20% by mass of campesterol, 10 to 20% by mass of stigmasterol, and 0 to 5% by mass of brassicasterol. Each composition of phytosterols derived from a variety of vegetable oils is indicated in Table 4 on page 324 of Non-Patent Document 1. Examples of commercially available phytosterols include PHYTOSTEROL, PHYTOSTEROL-S, PHYTOSTEROL-F any of which is available from Tama Biochemical Co., Ltd., PHYTOSTEROL-FKP available from Eisai Food Chemical Co., Ltd., RIKEN Plant STEROL available from Riken Vitamin Co., Ltd., ORYZA STEROL P and PC available from *Oryza* Oil & Fat Chemical Co., Ltd., NATURAL PHYTOSTEROLS (Non GMO Sunflower) available from Matrix Fine Sciences Pvt. Ltd. and ADVAS-TEROL 90S (Prill) available from Advanced Organic Materials, S.A. and the like.

The oil composition (A) in the present disclosure contains steradiene as a main component, has a phytosterol content of 20% by mass or less, and is liquid at 25° C. The content of steradiene in the oil composition (A) is usually 60% by mass or more, preferably 80% by mass or more, more preferably 90% by mass or more, particularly preferably 95% by mass or more. When phytosterol that is used as a raw material of steradiene remains in the oil composition, the residual phytosterol tends to reduce transparency of the oil composition. Therefore, the content of phytosterol in the oil composition is necessary to be 20% by mass or less, and it is preferably 10% by mass or less, more preferably 5% by mass or less. The oil composition has a viscosity at 25° C. of usually 20,000 to 60,000 mPa·s, preferably 35,000 to 50,000 mPa·s, and is a liquid having an appearance of clear and pale yellow in color.

The oil composition (A) of the present disclosure usually has a refractive index at 40° C. of 1.500 or more, preferably 1.510 or more, further preferably 1.520 or more. Such a large refractive index leads to significant improvement of gloss imparting property. The larger the phytosterol content, the refractive index tends to decrease. Hence, in view of maintaining a refractive index at a high level, the content of phytosterol in the oil composition is preferred to be 20% by mass or less, preferably 10% by mass or less, more preferably 5% by mass or less. The refractive index is measured using Abbe refractometer (ATAGO Co., Model: NAR-2T) in accordance with the general test method defined in Japanese Standards of Quasi-drug Ingredients.

The steradiene component that is contained as a main component in the oil composition (A) may be either a single steradiene or a mixture of two or more steradienes. Many of vegetable oils contain phytosterols including sitosterol as a main component. Therefore, the oil composition (A) is preferred to contain sitosteradiene derived from sitosterol as a main component in view of availability and economy. For example, the oil composition (A) is preferred to contain sitosteradiene in a range of 40 to 80% by mass.

The oil composition (A) may sometimes contain other compounds contained in a raw material and by-products in the dehydration reaction of phytosterol besides the steradiene component and phytosterol which is an unreacted raw material. Phytosterols derived from vegetable oils are difficult to completely separate phytosterol derivatives such as phytosterol fatty acid esters in the purification process thereof. Therefore, many commercial products of phytosterol contain up to about 10% by mass of the phytosterol derivatives. For example, when phytosterol derived from vegetable oils which is used as a raw material contains esters of oleic acid and phytosterol, the esters are difficult to completely remove in the purification process of the phytosterol, and remain as impurities in the purified phytosterol. Such phytosterol fatty acid esters remain in the oil composition obtained after the dehydration reaction of phytosterol due to having no relation to the dehydration reaction.

Further, upon synthesizing steradiene by dehydration of phytosterol, two molecules of phytosterol sometimes produce a phytosterol dimer as a by-product that has an ether bond formed between two hydroxyl groups located at each 3-C. Phytosterol fatty acid esters and phytosterol dimer may be contained as long as the effects of the embodiments of the present disclosure are not essentially impaired. When the content of these compounds in the oil composition is excessively large, crystals tend to precipitate, or the oil composition becomes pasty. Therefore, in the case of containing these compounds, the content of phytosterol fatty acid ester is preferably 30% by mass or less, more preferably 15% by mass or less, further more preferably 5% by mass or less, and the content of phytosterol dimer is preferably 30% by mass or less, more preferably 15% by mass or less, further more preferably 5% by mass or less.

The oil composition (A) can be used solely (for example, in the absence of oil (B)), and can be also used as an oil composition that contains the oil composition (A) and an oil (B) (for example, at a content that is above 0% by mass but below 30% by mass) being soluble therein (i.e., compatible therewith). The oil composition can be obtained by mixing the oil composition (A) and the oil (B). The mixing ratio is 70% by mass or more of the component (A) and 30% by mass or less of the component (B), preferably 90 to 75% by mass of the component (A) and 10 to 25% by mass of the component (B), more preferably 85 to 75% by mass of the component (A) and 15 to 25% by mass of the component (B). The larger the content of the component (B), storage stability of the oil composition is improved. However, when the content of the component (B) is excessively large, advantageous features of the component (A) are impaired.

The component (B) is an oil that is liquid at room temperature and can be used in the field of cosmetics and quasi-drugs. Examples thereof include, but not limited to, hydrocarbon oils such as liquid paraffin and squalane; ester oils such as diisostearyl malate, isopropyl myristate, cetyl 2-ethylhexanoate, caprylic/capric triglyceride, and triethylhexanoin; vegetable oils such as sunflower oil, olive oil, castor oil, macadamia nut oil, and jojoba oil; higher alcohols such as oleyl alcohol, octyldodecanol and isostearyl alcohol; higher fatty acids such as isostearic acid and oleic acid; silicone oils such as dimethylpolysiloxane and methyl phenyl polysiloxane; and the like. These oils may be used alone or in combination of two or more appropriately. Of these, ester oils and vegetable oils, in particular, cetyl 2-ethylhexanoate, tri-2-ethylhexanoate glyceryl and sunflower oil are preferably used in view of physical properties and cost.

The oil composition of the present disclosure, in particular, the oil composition composed of only the component (A) (for example, without oil (B) being present), however, in some embodiments such a composition may also contain an oil-soluble antioxidant (C). The component (A) is a very reactive substance due to having a conjugated double bond in its molecule. Therefore, there is a concern that the double bond may be involved in any reaction under conditions of high temperature and air atmosphere, which may cause deterioration of the original properties of the component (A). Incorporation of an appropriate amount of the antioxidant suppresses unexpected reactions, and contributes to improve storage stability of the oil composition (A).

The antioxidant (C) is not particularly limited as long as it is an oil-soluble antioxidant that is conventionally used in the field of cosmetics and quasi-drugs. Examples thereof include tocopherol and its derivatives, ascorbic acid fatty acid esters, dibutyl hydroxytoluene, butyl hydroxyanisole, rosemary extract, tea extract and the like. The tocopherol derivatives include isomers of tocopherol such as α-tocopherol, β-tocopherol, γ-tocopherol and δ-tocopherol; tocopherol acetate in which a hydroxyl group of tocopherol is modified with a fatty acid; tocotrienols having a basic structure of tocol; and the like.

If desired, the antioxidant (C) can be used in combination with a water-soluble antioxidant such as ascorbic acid, magnesium ascorbic acid-2-phosphate (trade name: APM, manufactured by Showa Denko), and sodium ascorbic acid 2-phosphate (trade name: APS, manufactured by Showa Denko). Among the antioxidant (C), tocopherol is preferably used in view of solubility and storage stability. The amount of the antioxidant (C) added to the component (A) depends on the compound used. It is preferably 0.01 to 5 parts by mass, more preferably 0.05 to 1 part by mass, further more preferably 0.1 to 0.5 part by mass relative to 100 parts by mass of the component (A).

<Production Process of Oil Composition>

The oil composition (A) of the present disclosure can be produced by using phytosterol derived from vegetable oils as a raw material, and dehydrating a hydroxyl group located at 3-C of the phytosterol to convert the hydroxyl group to a 3, 5-diene structure. The dehydration reaction can be carried out by heating the phytosterol in the absence or presence of a catalyst. The reaction temperature is usually 200 to 300° C., preferably 220 to 250° C., and the reaction time is 1 to 24 hours. The reaction is preferably carried out while removing water, which is generated by the dehydration reaction, out of the reactor. The reaction proceeds even without a catalyst, but, it is preferred to use a catalyst in view of reaction efficiency. Examples of the catalyst include inorganic acids such as sulfuric acid, hydrochloric acid and phosphoric acid; organic acids such as p-toluenesulfonic acid, methanesulfonic acid and boron trifluoride diethyl ether complex; and the like. Further, the reaction can be carried out in an appropriate solvent such as heptane, hexane, cyclohexane, toluene, and xylene.

After the dehydration reaction, an adsorbent such as activated clay, activated carbon, silica and alumina is added to the reaction liquid to adsorb the catalyst. Next, the treated liquid is filtered to remove the residual catalyst. Then, the desired oil composition (A) can be obtained by removing volatile components under reduced pressure as appropriate. In the case of carrying out the dehydration reaction without using a catalyst, the oil composition (A) can be obtained by drying the reaction liquid as needed without any operation to remove a catalyst.

In the case that the oil composition of the present disclosure is a mixture of the component (A) and the component (B), the mixture can be obtained, after purifying the component (A) in its production process, by adding the component (B) to the component (A), and homogeneously mixing both components. Of course, each component stored separately can be mixed appropriately to prepare the oil composition. In the case that the oil composition contains the oil-soluble antioxidant(C), it may be added to the component (A) in its production process followed by homogeneously mixing.

<Use of Oil Composition>

The oil composition of the present disclosure is an oil containing at least 70% by mass of the composition (A). The oil composition (A) is useful as a new oily material obtained from vegetable oils in the field, where phytosterols and phytosterol esters are used, since it is an oil being liquid at 25° C. and excellent in transparency. In particular, when formulated as an oily base in preparing an external preparation for skin, better gloss imparting property can be obtained without impairing moisture retention and feeling in use that are achieved by incorporation of phytosterol esters. Further, incorporation of the oil composition (A) enables it to prepare an external preparation for skin that is excellent in transparency, luster and moisture retention (i.e., low transepidermal water loss after application of external preparation for skin). Thus, the oil composition of the present disclosure is suitable as an oily base for external preparation for skin.

<External Preparation for Skin Comprising the Oil Composition>

The external preparation for skin of the present disclosure can be prepared according to conventional methods except for including the oily base that contains at least 70% by mass of the oil composition (A). The form of the external preparation for skin is not particularly limited, and may be any of oily type, aqueous type and emulsion type. Examples of the external preparation for skin include skin care cosmetics such as milky lotion, cream, lotion, pack and cleaning; cosmetics such as lipstick and makeup cosmetic; hair cosmetics such as hair rinse, hair conditioner, hair setting agents and hair dyes; Quasi-drugs such as ointment, dispersion, cream and liquid for external use; and the like. Examples of dosage form include, but not limited to, solid, paste, mousse, gel, powder, solution, microemulsion, emulsion, powder dispersion, multilayered, and the like.

In the case of preparing an external preparation for skin having an emulsion type such as milky lotion and cream, the type is not particularly limited, and examples thereof include O/W (oil-in-water), W/O (water-in-oil), W/O/W (water-in-oil-in-water), O/W/O (oil-in-water-oil), and the like.

The content of the oily base in the external preparation for skin of the present disclosure depends on its type and dosage form, and is usually 0.1 to 60% by mass, preferably 0.5 to 50% by mass, more preferably 1 to 40% by mass. When the content of the oil base is too small, it becomes difficult to obtain the effect of improving gloss, transparency and moisture retention.

The external preparation for skin of the present disclosure may contain other ingredients usually used in the formulation of cosmetics and quasi-drugs within a range not to impair the effects of the present disclosure beside the above oily base. Examples of the ingredients include water such as purified water, spring water and deep water, oils other than the above oily base, surfactants, metal soaps, gelling agents, powders, alcohols, water-soluble polymers, film-forming agents, resins, ultraviolet protective agents, clathrates, antimicrobial agents, perfumes, deodorants, salts, PH adjusting agents, cooling agents, animal-microbial extract, plant extracts, blood circulation promoters, astringents, anti-seborrhoeic agents, active oxygen scavengers, cell activating agents, humectants, keratolytic agents, enzymes, hormones, vitamins, and the like. These ingredients may be added alone or in combination of two or more.

As the oil other than the above oily base, any oil that is commonly used in cosmetics can be used regardless of the type of oils such as natural oil or synthetic oil, and properties such as solid, semi-solid and liquid. Examples thereof include hydrocarbons, waxes, fatty acids, higher alcohols, ester oils, silicone oils, fluorine-based oils, and the like. As the surfactant, any of anionic, cationic, nonionic or amphoteric surfactants can be used. As the powder, any of inorganic powders, organic powders and pigments that are commonly used in cosmetics can be used regardless of their shape such as spherical, needle and plate, particle size such as fume, fine particle and pigment-grade, and particle structure such as porous and non-porous.

The external preparation for skin of the present disclosure can be prepared according to conventional methods. For example, when preparing a lipstick, the product can be obtained by dispersing a colorant in an oil using a roller mill, adding the resultant dispersion to a solution prepared by heating other components and mixing well the resultant mixture, filtering the mixture to take a filtrate, pouring the filtrate into a mold at a high temperature, cooling it to form a solid material, and filling the solid material into a container. Also, when preparing a lip gloss, the product can be obtained by dissolving all ingredients with heating, mixing well the resultant solution, filtering the solution, pouring the filtrate into a mold at a high temperature, cooling it to form a solid material, and filling the solid material into a container.

Furthermore, when preparing a hair wax, the product can be obtained by respectively heating an oil phase containing an oil component and a surfactant, and an aqueous phase containing a neutralizing agent, then slowly adding the aqueous phase to the oil phase with stirring, adding an aqueous phase containing a thickening agent followed by mixing, then adding an aqueous phase containing a neutralizing agent followed by mixing, and cooling the mixture.

EXAMPLES

Hereinafter, the embodiments of the present disclosure will be further described with reference to Examples, but the present invention is not limited by these Examples. The terms "parts" and "%" in Examples represent "parts by mass" and "% by mass" unless otherwise specified.

The conditions for measuring physical properties and the evaluation methods of the oil composition in the following Examples and Comparative Examples are as follows.
(1) Composition analysis: Gas chromatographic analysis using GC2010 (Shimadzu Corporation).
(2) Transparency: Visual observation.
(3) Refractive index: Measured at 40° C. in accordance with the refractive index measuring method of Japanese Standards of Quasi-drug Ingredients using Abbe refractometer (ATAGO Co., Ltd. Model: NAR-2T),
(4) Hydroxyl value: Measured in accordance with Japanese Standards of Quasi-drug Ingredients 2006.
(5) Viscosity: Measured in accordance with the second method of viscosity measuring method defined in Japanese Standards of Quasi-drug Ingredients 2006 using BM type viscometer (BROOKFIELD Corporation, Model: DV3T).
(Evaluation of Transparency)
A sample heated to 80° C. in a beaker of 100 ml was allowed to stand one day at room temperature. Then, its appearance was assessed in four grades below.

A: Transparent
B: Slightly turbid
C: Turbid
D: Opaque
(Evaluation of Lip Gloss)
Gloss: Measuring the refractive index as an indication of gloss of the lip gloss, gloss was assessed in four grades below based on the value obtained.
A: Refractive index of 1.445 or more
B: Refractive index of 1.440 to 1.445
C: Refractive index of 1.435 to 1.440
D: Refractive index of less than 1.435
Adhesion: After applying a predetermined amount of the sample to the left back of the hand, adhesion was assessed in four grades below. Panelists are five, and evaluation score is an average value of scores obtained by 5 panelists.
Evaluation Criteria
Score 4: Very good
Score 3: Good
Score 2: Slightly Good
Score 1: Poor
Evaluation
A: 3.5 or more
B: 2.5 to 3.5
C: 1.5 to 2.5
D: less than 1.5
(Evaluation of Hair Wax)
After spreading a sample of 5 g on the palm of hand, the sample was stroked to hair to make a hair set. As to hair gloss, condition of whole hair, and condition of hair bundle applied with the sample (feeling of hair bundle), five panelists assessed in four grades according to the evaluation criteria below. Evaluation is based on an average value of scores obtained by 5 panelists.
Evaluation Criteria
Score 4: Very good
Score 3: Good
Score 2: Slightly good
Score 1: Poor
Evaluation
A: 3.5 or more
B: 2.5 to 3.5
C: 1.5 to 2.5
D: less than 1.5
(Evaluation of Cream: TEWL: Trans Epidermal Water Loss)
A sample of 0.1 g was dropped to the inner arm, and applied to an area of 3 cm×3 cm (vertical and horizontal) of the inner arm by reciprocating the index finger ten times left and right, respectively. After remaining in a room having a temperature of 20° C. and a humidity of 50% for 30 minutes, trans epidermal water loss (TEWL) was measured using Cutometer DUAL MPA580 (Courage+Khazaka electronic GmbH). Then, TEWL was measured at the time when 4 hours or 8 hours elapsed as it was. Evaluation of TEWL is expressed as an index when the value of TEWL before application is 100.

Example 1

As a raw material, phytosterol that was solid at room temperature, and obtained from soybean oil and rapeseed oil was prepared. The phytosterol contained 44.8% of β-sitosterol, 27.6% of campesterol, 17.2% of stigmasterol, 6.4% of brasicasterol, 1% of fatty acid ester of phytosterol as an impurity and 3% of water. In a reactor of 500 mL equipped with a stirrer, a thermometer and a nitrogen blowing tube, 400 g (1.0 mole) of the above phytosterol and 0.4 g of p-toluenesulfonic acid monohydrate were charged, and the mixture was heated to 220 to 240° C. under a nitrogen stream for 8 hours to carry out the reaction while removing generated water. After cooling the reaction liquid, activated clay was added to adsorb p-toluenesulfonic acid monohydrate, and then the reaction liquid was filtered to obtain 351 g of a pale yellow and transparent liquid product. The yield of the liquid product was 87.8%, and the production amount of steradiene was 331 g. This product had a composition composed of 96% of mixed steradienes produced by dehydration reaction of β-sitosterol, campesterol, stigmasterol and brassicasterol, 3% of residual phytosterol, and 1% of phytosterol ester contained in the raw material, and had a hydroxyl value of 5.2, a refractive index at 40° C. of 1.5230, and a viscosity at 25° C. of 41,300 mPa·s. The UV-C absorption capacity (maximum absorption at a wavelength of 235 nm) of this oily product was measured using UV-1800 available from Shimadzu Corporation. The oily product had a molar absorption coefficient e of 34,000, and exhibited extremely high absorption capacity. Hereinafter, this oily composition is referred to as "Oily Base 1."

Example 2

A pale yellow and transparent liquid product was obtained in an amount of 355 g according to the same manner as in Example 1 except for shortening the reaction time to 6 hours. The yield of the liquid product was 88.8%, and the production amount of steradiene was 320 g. Properties of the product are shown in Table 1. Hereinafter, this oily composition is referred to as "Oily Base 2."

Example 3

A pale yellow and transparent liquid product was obtained in an amount of 350 g according to the same manner as in Example 1 except for increasing the amount of p-toluenesulfonic acid monohydrate to 1.2 g. The yield of the liquid product was 88.8%, and the production amount of steradiene was 320 g. Properties of the product are shown in Table 1. Hereinafter, this oily composition is referred to as "Oily Base 3."

Example 4

A pale yellow and transparent oil mixture was prepared by mixing 67 parts of Oily Base 1 with 15 parts of fatty acid ester of phytosterol that is an ester of phytosterol derived from sunflower oil and fatty acids, and has a purity of 90%. The oil mixture was composed of 82% of steradienes, 4% of residual phytosterols, and 14% of phytosterol esters. Properties of the oil mixture are shown in Table 1. Hereinafter, this oily composition is referred to as "Oily Base 4."

Comparative Example 1

A pasty product was obtained in an amount of 348 g according to the same manner as in Example 1 except for increasing the amount of p-toluenesulfonic acid monohydrate to 2 g. The yield of the pasty product was 87.0%, and the production amount of steradienes was 205 g. Properties of the oily product are shown in Table 1. Hereinafter, this oily composition is referred to as "Comparative Oily Base 1" or "Oily Base C1."

Comparative Example 2

A solid product was obtained in an amount of 357 g according to the same manner as in Example 1 except for changing the reaction temperature to 160° C. to 180° C. The yield of the solid product was 89.3%, and the production amount of steradienes was 204 g. Properties of the oily product are shown in Table 1. Hereinafter, this oily composition is referred to as "Comparative Oily Base 2" or "Oily Base C1."

TABLE 1

|  | Example | | | | Comparative Example | |
| --- | --- | --- | --- | --- | --- | --- |
|  | 1 | 2 | 3 | 4 | 1 | 2 |
| Oily Base No. | 1 | 2 | 3 | 4 | C1 | C2 |
| Composition (%) | | | | | | |
| Steradiene | 96 | 90 | 81 | 82 | 59 | 57 |
| Residual Phytosterol | 3 | 9 | 4 | 4 | 3 | 39 |
| Phytosterol fatty acid ester | 1 | 1 | 1 | 14 | 1 | 1 |
| Phytosterol dimer | 0 | 0 | 14 | 0 | 37 | 3 |
| Total | 100 | 100 | 100 | 100 | 100 | 100 |
| Property of Oil Composition | | | | | | |
| Hydroxyl value | 5.2 | 17.2 | 7.2 | 7.1 | 5.5 | 69.7 |
| Refractive index (40° C.) | 1.5230 | 1.5205 | 1.5110 | 1.5130 | — | — |
| Transparency | A | B | B | B | C | D |
| Appearence (25° C.) | Liquid | Liquid | Liquid | Liquid | Pasty | Solid |
| Viscosity (25° C.) mPa·s | 41,300 | 44,900 | 49,600 | 39,800 | — | — |

Examples 5 to 8 and Comparative Examples 3 to 8

<Lip Gloss>

A lip gloss of the formulation shown in Table 2 was prepared according to the following procedure, and was evaluated as to refractive index, gloss, and adhesion. For comparison, a lip gloss containing no steradiene oil and a lip gross containing a commercial fatty acid ester of phytosterol in place of steradiene oil were evaluated in the same manner. The results are shown in Table 2.

(Preparation Procedure)

(1) Ingredients contained in Phase (A) of Table 2 were heated to about 90° C., and mixed homogeneously.

(2) The mixed liquid prepared in the above (1) was filled into a container to make a lip gloss.

TABLE 2

| Phase | Ingredient | Example 5 | Example 6 | Example 7 | Example 8 | Comparative Example 3 | Comparative Example 4 | Comparative Example 5 | Comparative Example 6 | Comparative Example 7 | Comparative Example 8 |
|---|---|---|---|---|---|---|---|---|---|---|---|
| A | Carnauba wax (*1) | 5.0 | 5.0 | 5.0 | 5.0 | 5.0 | 5.0 | 5.0 | 5.0 | 5.0 | 5.0 |
|  | Microcrystalline wax (*2) | 4.0 | 4.0 | 4.0 | 4.0 | 4.0 | 4.0 | 4.0 | 4.0 | 4.0 | 4.0 |
|  | Polyethylene (*3) | 8.0 | 8.0 | 8.0 | 8.0 | 8.0 | 8.0 | 8.0 | 8.0 | 8.0 | 8.0 |
|  | Triethylhexanoin (*4) | 63.0 | 63.0 | 63.0 | 63.0 | 63.0 | 63.0 | 63.0 | 63.0 | 63.0 | 83.0 |
|  | Oily Base |  |  |  |  |  |  |  |  |  |  |
|  | 1 | 20.0 |  |  |  |  |  |  |  |  |  |
|  | 2 |  | 20.0 |  |  |  |  |  |  |  |  |
|  | 3 |  |  | 20.0 |  |  |  |  |  |  |  |
|  | 4 |  |  |  | 20.0 |  |  |  |  |  |  |
|  | C1 |  |  |  |  | 20.0 |  |  |  |  |  |
|  | C2 |  |  |  |  |  | 20.0 |  |  |  |  |
|  | Commercial Product A (*5) |  |  |  |  |  |  | 20.0 |  |  |  |
|  | Commercial Product B (*6) |  |  |  |  |  |  |  | 20.0 |  |  |
|  | Commercial Product C (*7) |  |  |  |  |  |  |  |  | 20.0 |  |
|  | None |  |  |  |  |  |  |  |  |  | — |
|  | Evaluation |  |  |  |  |  |  |  |  |  |  |
|  | Refractive index | A | B | B | B | C | D | C | C | C | D |
|  | Adhesion | A | A | B | B | C | C | B | C | B | D |

(*1) Purified Carnuba Wax R-100 (Yokozeki Fat & Oil Co., Ltd.)
(*2) Purified Microcrystalline Wax (Nikko Rika Corporation)
(*3) PERFORMALENE 400 (New Phase Technologies)
(*4) Triethylhexanoin (The Nissin Oillio Group, Ltd.)
(*5) Commercial product A (Phytosteryl Isostearyl Dimer Dilinoleate)
(*6) Commercial product B (Phytosteryl/Isostearyl/Cetyl/Stearyl/Behenyl Dimer Dilinoleate
(*7) Commercial product C (Phytosteryl/Octyldodecyl Lauroyl Glutamate)

Lip glosses using any of Oily Bases 1 to 4 of the present disclosure are excellent in gloss due to a large refractive index, and also exhibit good performance in adhesion (see Examples 5 to 8). In contrast, lip glosses using Comparative Oily Bases 1 to 2 or the commercial fatty acid ester of phytosterol have improved property in adhesion as compared with the lip gloss containing no oily base as shown in Comparative Example 8, but are insufficient in gloss since the refractive indices are smaller as compared with Examples of the present disclosure (see Comparative examples 3 to 7).

Examples 9 to 12 and Comparative Examples 9 to 14

<Hair Wax>

A hair wax of the formulation shown in Table 3 was prepared according to the following procedure, and was evaluated as to gloss, condition of whole hair and feeling of hair bundle. For comparison, hair waxes containing a commercial phytosterol derivative were evaluated in the same manner. The results are shown in Table 3.

(Preparation Procedure)

(1) Ingredients contained in Phase (A) and Phase (B) of Table 3 were heated to about 70° C., and mixed homogeneously.

(2) Ingredients contained in Phase (C) and Phase (D) of Table 3 were added to the mixture prepared in the above (1), and mixed homogeneously.

(3) The mixture was cooled to 35° C. with stirring.

(4) The mixture obtained in the above (3) was filled into a container to make a hair wax.

TABLE 3

| Phase | | Ingredient | Example 9 | Example 10 | Example 11 | Example 12 | Comparative Example 9 | Comparative Example 10 | Comparative Example 11 | Comparative Example 12 | Comparative Example 13 | Comparative Example 14 |
|---|---|---|---|---|---|---|---|---|---|---|---|---|
| A | A | Purified water | 15.0 | 15.0 | 15.0 | 15.0 | 15.0 | 15.0 | 15.0 | 15.0 | 15.0 | 20.0 |
|  | A | Triethanolamine | 1.0 | 1.0 | 1.0 | 1.0 | 1.0 | 1.0 | 1.0 | 1.0 | 1.0 | 1.0 |
|  | A | Butylene glycol | 3.0 | 3.0 | 3.0 | 3.0 | 3.0 | 3.0 | 3.0 | 3.0 | 3.0 | 3.0 |
|  | A | Phenoxyethanol | 0.5 | 0.5 | 0.5 | 0.5 | 0.5 | 0.5 | 0.5 | 0.5 | 0.5 | 0.5 |
| B | B | Sunflower seed wax (*8) | 15.0 | 15.0 | 15.0 | 15.0 | 15.0 | 15.0 | 15.0 | 15.0 | 15.0 | 15.0 |
|  | B | Microcrystalline wax | 5.0 | 5.0 | 5.0 | 5.0 | 5.0 | 5.0 | 5.0 | 5.0 | 5.0 | 5.0 |
|  | B | Stearic acid | 4.0 | 4.0 | 4.0 | 4.0 | 4.0 | 4.0 | 4.0 | 4.0 | 4.0 | 4.0 |
|  | B | Stearyl alcohol | 2.0 | 2.0 | 2.0 | 2.0 | 2.0 | 2.0 | 2.0 | 2.0 | 2.0 | 2.0 |
|  | B | Dimethicone (*9) | 9.0 | 9.0 | 9.0 | 9.0 | 9.0 | 9.0 | 9.0 | 9.0 | 9.0 | 9.0 |

TABLE 3-continued

| Phase | | Ingredient | Example | | | | Comparative Example | | | | | |
|---|---|---|---|---|---|---|---|---|---|---|---|---|
| | | | 9 | 10 | 11 | 12 | 9 | 10 | 11 | 12 | 13 | 14 |
| | B | Cetyl ethylhexanoate | 8.0 | 8.0 | 8.0 | 8.0 | 8.0 | 8.0 | 8.0 | 8.0 | 8.0 | 8.0 |
| | B | Sorbitan stearate | 1.0 | 1.0 | 1.0 | 1.0 | 1.0 | 1.0 | 1.0 | 1.0 | 1.0 | 1.0 |
| | B | Seteth-20 | 6.0 | 6.0 | 6.0 | 6.0 | 6.0 | 6.0 | 6.0 | 6.0 | 6.0 | 6.0 |
| | B | Oily Base | | | | | | | | | | |
| | | 1 | 5.0 | | | | | | | | | |
| | | 2 | | 5.0 | | | | | | | | |
| | | 3 | | | 5.0 | | | | | | | |
| | | 4 | | | | 5.0 | | | | | | |
| | | C1 | | | | | 5.0 | | | | | |
| | | C2 | | | | | | 5.0 | | | | |
| | | Commercial Product A (*5) | | | | | | | 5.0 | | | |
| | | Commercial Product B (*6) | | | | | | | | 5.0 | | |
| | | Commercial Product C (*7) | | | | | | | | | 5.0 | |
| | | None | | | | | | | | | | — |
| C | C | Carbomer (2% aqueous solution) (*10) | 20.0 | 20.0 | 20.0 | 20.0 | 20.0 | 20.0 | 20.0 | 20.0 | 20.0 | 20.0 |
| D | D | Triethanolamine | 0.5 | 0.5 | 0.5 | 0.5 | 0.5 | 0.5 | 0.5 | 0.5 | 0.5 | 0.5 |
| | D | Purified water | 5.0 | 5.0 | 5.0 | 5.0 | 5.0 | 5.0 | 5.0 | 5.0 | 5.0 | 5.0 |
| | | Evaluation | | | | | | | | | | |
| | | Gloss | A | A | A | B | C | C | C | C | C | D |
| | | Condition of whole hair | B | B | B | B | B | B | C | C | B | D |
| | | Feeling of hair bundle | A | B | B | B | C | C | B | C | C | D |

(*8) Purified sunflower wax (Yokozeki Fat & Oil Co., Ltd.)
(*9) KF-96A-6cs (Shin-Etsu Chemical Co., Ltd.)
(*10) NTC-CARBOMER 380 (Nikko Chemicals o., Ltd.)

Hair waxes using any of Oily Bases 1 to 4 of the present disclosure are excellent in gloss, and also exhibit good performance in feeling of hair bundle (see Examples 9 to 12). In contrast, hair waxes using any of Comparative Oily Bases 1 to 2 or the commercial fatty acid ester of phytosterol tend to have improved property in condition of whole hair and feeling of hair bundle as compared with the hair wax containing no oily base as shown in Comparative Example 14, but are insufficient in gross as compared with Examples of the present disclosure (see Comparative examples 9 to 14).

Examples 13 to 16 and Comparative Examples 15 to 20

<Cream>
An oil-in-water cream of the formulation shown in Table 4 was prepared according to the following procedure, and TEWL (Trans Epidermal Water Loss) was measured before application, immediately after application, that is, 30 minutes later from application, 4 hours later from application, and 8 hours later from application, respectively. For comparison, oil-in-water creams containing a commercial phytosterol derivative were evaluated in the same manner. The results are shown in Table 4.

(Preparation Procedure)
(1) Ingredients contained in Phase (A) of Table 4 were heated to about 70° C., followed by adding thereto components contained in Phase (B) and mixing homogeneously.
(2) Ingredients contained in Phase (C) and Phase (D) of Table 4 were added to the mixture prepared in the above (1), and mixed homogeneously.
(3) The mixture obtained in the above (2) was filled into a container to make a cream.

TABLE 4

| Phase | | Ingredient | Example | | | | Comparative Example | | | | | |
|---|---|---|---|---|---|---|---|---|---|---|---|---|
| | | | 13 | 14 | 15 | 16 | 15 | 16 | 17 | 18 | 19 | 20 |
| A | A | PEG-60 hydrogenated cstor oil (*11) | 0.5 | 0.5 | 0.5 | 0.5 | 0.5 | 0.5 | 0.5 | 0.5 | 0.5 | 0.5 |
| | | Oily Base | | | | | | | | | | |
| | | 1 | 2.0 | | | | | | | | | |
| | | 2 | | 2.0 | | | | | | | | |
| | | 3 | | | 2.0 | | | | | | | |
| | | 4 | | | | 2.0 | | | | | | |
| | | C1 | | | | | | | | | | 2.0 |

TABLE 4-continued

| | | | Example | | | | Comparative Example | | | | | |
|---|---|---|---|---|---|---|---|---|---|---|---|---|
| Phase | | Ingredient | 13 | 14 | 15 | 16 | 15 | 16 | 17 | 18 | 19 | 20 |
| | | C2 | | | | | | 2.0 | | | | |
| | | Commercial Product A (*5) | | | | | | | 2.0 | | | |
| | | Commercial Product B (*6) | | | | | | | | 2.0 | | |
| | | Commercial Product C (*7) | | | | | | | | | 2.0 | |
| | | None | | | | | | | | | | — |
| B | B | Purified water | 60.0 | 60.0 | 60.0 | 60.0 | 60.0 | 60.0 | 60.0 | 60.0 | 60.0 | 60.0 |
| C | C | Carbomer (2% aqueous solution) (*10) | 25.0 | 25.0 | 25.0 | 25.0 | 25.0 | 25.0 | 25.0 | 25.0 | 25.0 | 25.0 |
| D | D | Potassium hydroxide | 0.25 | 0.25 | 0.25 | 0.25 | 0.25 | 0.25 | 0.25 | 0.25 | 0.25 | 0.25 |
| | D | Purified water | 12.25 | 12.25 | 12.25 | 12.25 | 12.25 | 12.25 | 12.25 | 12.25 | 12.25 | 14.25 |
| | | Evaluation of TEWL | | | | | | | | | | |
| | | Before application | 100 | 100 | 100 | 100 | 100 | 100 | 100 | 100 | 100 | 100 |
| | | 30 min. later from allicaation | 255 | 200 | 256 | 175 | 211 | 180 | 266 | 283 | 139 | 167 |
| | | 4 hous later from application | 90 | 93 | 101 | 120 | 110 | 98 | 96 | 93 | 112 | 114 |
| | | 8 hours later from application | 83 | 87 | 89 | 89 | 89 | 91 | 96 | 107 | 101 | 100 |

(*11) NIKKOLHOD-60 (Nikko Chemicals Co., Ltd.)

The creams using any of Oily Bases 1 to 4 of the present disclosure are excellent in moisture retention at the time of 8 hour later from application as compared with the cream of Comparative Example 20 containing no oily base or the creams of Comparative Examples 17 to 19 containing a commercial fatty acid ester of phytosterol (Example 13 to 16). They are also excellent in gloss and feeling of hair bundle.

Example 17

An oil composition was prepared by blending 80 parts of Oily Base 1 obtained in Example 1 with 20 parts of sunflower oil (Product name: HIOLEC SUNFLOWER OIL available from Yokozeki Fat & Oil Co., Ltd.) at room temperature followed by homogeneously mixing. Hereinafter, the oil composition is referred to as "Oily Base 5." The Oily Base 5 was a liquid having a refractive index at 40° C. of 1.5078, and a viscosity at 25° C. of 2,800 mPa s, and its evaluation result of transparency was A. The Oil Base 5 was allowed to stand for 180 days at room temperature to observe change of appearance. The appearance did not cause any special change. This result indicated that the Oil Base 5 was excellent in storage stability.

A lip gloss was prepared in the same manner as in Example 5 except for using the Oily Base 5 in place of the Oily Base 1, and assessed as to gloss and adhesion. Its evaluation result of gloss was B, and its evaluation result of adhesion was also B. As seen from the results, the lip gloss using the Oily Base 5 is good in gloss and adhesion, but did not extend to the level of the lip gloss of Example 5 using the Oily Base 1.

Comparative Example 21

An oil composition was prepared by blending 60 parts of Oily Base 1 obtained in Example 1 with 40 parts of sunflower oil (Product name: HIOLEC SUNFLOWER OIL available from Yokozeki Fat & Oil Co., Ltd.) at room temperature followed by homogeneously mixing. Hereinafter, the oil composition is referred to as "Comparative Oily Base 3." The Comparative Oily Base 3 was a liquid having a refractive index at 40° C. of 1.4592, and a viscosity at 25° C. of 580 mPa·s, and its evaluation result of transparency was A. A lip gloss was prepared in the same manner as Example 5 except for using the Comparative Oily Base 3 in place of the Oily Base 1, and assessed as to gloss and adhesion. Its evaluation result of gloss was C, and its evaluation result of adhesion was also C. As seen from the results, the lip gloss using the Comparative Oily Base 3 was greatly inferior in gloss and adhesion as compared with the lip glosses of Examples 5 and 17.

Example 18

To 100 parts of the Oily Base 1 obtained in Example 1, 0.2 parts of tocopherol were added as an antioxidant followed by homogeneously mixing to prepare "Oily Base 6." Similarly, "Oily Base 7" was prepared by adding 1.0 part of tocopherol to 100 parts of the Oily Base 1 followed by homogeneously mixing. Both of the Oily Base 6 and the Oily Base 7 were clear liquid compositions, and had a refractive index at 40° C. of 1.5201. The Oily Base 6 and the Oily Base 7 had a viscosity at 25° C. of 40,500 mPa·s and 35,700 mPa·s, respectively.

The Oily Base 6 and the Oily Base 7 were allowed to stand for 180 days at room temperature to observe change of appearance. Each of oily bases did not cause any special change in color. This result indicated that these oily bases were excellent in storage stability. Further, lip glosses prepared in the same manner as in Example 5 except for using the Oily Base 6 or the Oily Base 7 in place of the Oily Base 1 exhibited almost the same performance as the lip gloss of Example 5.

According to the present disclosure, there is provided an oil composition that is excellent in safety, color, transparency and gloss imparting property, and is suitable as a liquid oily base to prepare an external preparation for skin. Use of the oil composition as an oily base of an external preparation for skin makes the oily base to be readily handled upon preparing the external preparation, and the external preparation for skin thus obtained is excellent in adhesion and moisture retention as well as gloss.

What is claimed is:

1. An oil composition comprising:
   70 to 100% by mass of an oil composition (A) that contains, as a main component, a steradiene having a 3,5-conjugated diene structure obtained by dehydrating a hydroxyl group located at 3-position of phytosterol, wherein the oil composition (A)
      has a phytosterol content of 20% by mass or less, and is liquid at 25° C.; and
   0 to 30% by mass of an oil (B) that is soluble in the oil composition (A).

2. The oil composition according to claim 1, wherein the oil composition (A) has
   a steradiene content of 60% by mass or more,
   a phytosterol fatty acid ester content of 30% by mass or less and
   a phytosterol dimer content of 30% by mass or less.

3. The oil composition according to claim 1, wherein the oil composition (A) has
   a steradiene content of 80% by mass or more,
   a phytosterol content of 10% by mass or less,
   a phytosterol fatty acid ester content of 15% by mass or less and
   a phytosterol dimer content of 15% by mass or less.

4. The oil composition according to claim 1, wherein the steradiene contains a citosteradiene content of 40 to 80% by mass.

5. The oil composition according to claim 1, wherein the oil composition (A) has a viscosity at 25° C. of 20,000 to 60,000 mPa·s.

6. The oil composition according to claim 1, wherein the oil composition (A) has a refractive index at 40° C. of 1.500 or more.

7. The oil composition according to claim 1, further comprising 0.01 to 5% by mass of an oil-soluble antioxidant (C) relative to 100 parts by mass of the oil composition (A).

8. The oil composition according to claim 1, wherein the oil (B) is at least one selected from the group consisting of hydrocarbon oils, ester oils, vegetable oils, higher alcohols, higher fatty acids, and silicone oils.

9. A method for producing an oil composition according claim 1, wherein a phytosterol is heated in the presence or absence of a dehydration catalyst, and optionally mixed with the oil (B) and/or an oil-soluble antioxidant (C).

10. An oily base for producing an external preparation for skin consisting essentially of the oil composition according to claim 1.

11. An external preparation for skin comprising the oily base according to claim 10.

12. The external preparation for skin according to claim 11, wherein it is a cosmetic.

13. The external preparation for skin according to claim 12, wherein the cosmetic is a hair wax, a lipstick or a lip gloss.

* * * * *